(12) United States Patent
Shute et al.

(10) Patent No.: US 12,245,891 B2
(45) Date of Patent: Mar. 11, 2025

(54) IMAGING OF A BODY PART USING SOUNDS

(71) Applicant: Cardiac Pacemakers, Inc., St. Paul, MN (US)

(72) Inventors: Jonathan B. Shute, Minnetonka, MN (US); Pramodsingh H. Thakur, Woodbury, MN (US); Bin Mi, Arden Hills, MN (US); Bryan A. Clark, St. Paul, MN (US); Qi An, Blaine, MN (US); Ramesh Wariar, Blaine, MN (US); Krzysztof Z. Siejko, Maple Grove, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 1088 days.

(21) Appl. No.: 16/238,934

(22) Filed: Jan. 3, 2019

(65) Prior Publication Data
US 2019/0223839 A1    Jul. 25, 2019

Related U.S. Application Data

(60) Provisional application No. 62/613,394, filed on Jan. 3, 2018.

(51) Int. Cl.
*A61B 8/08* (2006.01)
*A61B 5/11* (2006.01)
(Continued)

(52) U.S. Cl.
CPC .......... *A61B 8/5207* (2013.01); *A61B 5/1102* (2013.01); *A61B 5/1114* (2013.01);
(Continued)

(58) Field of Classification Search
CPC ... A61B 8/5207; A61B 5/1102; A61B 5/1114; A61B 5/349; A61B 7/04; A61B 8/00;
(Continued)

(56) References Cited

U.S. PATENT DOCUMENTS 6,978,182 B2   12/2005  Mazar et al.
7,338,436 B1 *  3/2008  Snell .................... A61F 2/2481
                                                           600/16
(Continued)

FOREIGN PATENT DOCUMENTS

CN      103052353 A     4/2013
WO      2017/141165 A1  8/2017

OTHER PUBLICATIONS

Nogata et al., Novel technique for Visualizing Heart Motion without using Ultrasonic Cardiography, IEEE-EMBS, BHI 2012, pp. 249-252. (Year: 2012).*

(Continued)

*Primary Examiner* — Sanjay Cattungal
(74) *Attorney, Agent, or Firm* — Faegre Drinker Biddle & Reath LLP

(57) ABSTRACT

Embodiments of the present disclosure relate to imaging a body part using sounds. In embodiments, a system comprises a motion sensor and a processing device communicatively coupled to the motion sensor. The motion sensor is configured to sense an acceleration wave produced by a sound emitted by a source and generate acceleration measurements in response to sensing the acceleration wave, wherein the source is associated with the body part of a subject. The processing device is configured to receive the acceleration measurements and determine a location of the source using a location of the motion sensor and the acceleration measurements. In addition, the processing device is configured to image the body part of the subject using the (Continued)

determined location of the source and the acceleration measurements.

16 Claims, 7 Drawing Sheets

(51) Int. Cl.
    *A61B 5/349*     (2021.01)
    *A61B 7/04*     (2006.01)
    *A61B 8/00*     (2006.01)
    *A61B 7/00*     (2006.01)

(52) U.S. Cl.
    CPC .............. *A61B 5/349* (2021.01); *A61B 7/04* (2013.01); *A61B 8/00* (2013.01); *A61B 8/0883* (2013.01); *A61B 8/543* (2013.01); *A61B 7/00* (2013.01); *A61B 2562/0219* (2013.01)

(58) Field of Classification Search
    CPC ......... A61B 8/0883; A61B 8/543; A61B 7/00; A61B 2562/0219
    See application file for complete search history.

(56) References Cited

U.S. PATENT DOCUMENTS

| | | |
|---|---|---|
| 2008/0281214 A1 | 11/2008 | Elle et al. |
| 2009/0036790 A1* | 2/2009 | Landesberg ...... A61M 16/0069 600/529 |
| 2010/0081948 A1 | 4/2010 | Pastore et al. |
| 2011/0048103 A1 | 3/2011 | Su et al. |
| 2011/0105932 A1 | 5/2011 | Bauer et al. |
| 2013/0131525 A1 | 5/2013 | Yin et al. |
| 2015/0038856 A1* | 2/2015 | Houlton ............... A61B 5/6826 600/484 |
| 2015/0111657 A1* | 4/2015 | Shibuya ................. G06V 40/23 473/409 |
| 2016/0166880 A1* | 6/2016 | Nakajima .......... G06Q 10/0639 434/247 |
| 2016/0345870 A1* | 12/2016 | Ichikawa ............. A61B 5/0024 |
| 2018/0214030 A1* | 8/2018 | Migeotte ............ A61B 5/02028 |
| 2018/0235518 A1* | 8/2018 | Barton ................. A61B 5/0024 |
| 2020/0129126 A1* | 4/2020 | Kovoor ................. A61B 5/6852 |
| 2021/0290109 A1* | 9/2021 | Gaddipati ............. A61B 5/1113 |

OTHER PUBLICATIONS

International Search Report and Written Opinion issued in PCT/US2019/012154, mailed Mar. 15, 2019, 29 pages.

Siejko, K. Z., et al. (Mar. 2013). Feasibility of Heart Sounds Measurements from an Accelerometer Within an ICD Pulse Generator. Pace, 36:334-346.

\* cited by examiner

IMAGING OF A BODY PART USING SOUNDS

CROSS-REFERENCE TO RELATED APPLICATION

This application claims priority to Provisional Application No. 62/613,394, filed Jan. 3, 2018, which is herein incorporated by reference in its entirety.

TECHNICAL FIELD

The presently disclosed subject matter relates to devices and methods for imaging one or more parts of a subject. More specifically, the disclosed subject matter relates to devices, systems, and methods for imaging one or more parts of a subject using heart sounds.

BACKGROUND

The opening and closing of valves, as well as aspects of the flow of blood through the heart, produce vibrations known as heart sounds (sometimes abbreviated as "HS" herein). Heart sounds may be measured and used to indicate the heart's mechanical activities. Additionally, measurements performed with simultaneously recorded ECG and heart sounds provide for quantitative indications of the electro-mechanical association.

SUMMARY

Embodiments disclosed herein use heart sounds to image the heart. While the embodiments are discussed in relation to using heart sounds to image a heart, heart sounds or sounds produced by a thumper or another organ may be used to image parts of the body other than the heart. Example embodiments include but are not limited to the following examples.

In an Example 1, a system for imaging a body part, comprising: a motion sensor configured to sense an acceleration wave emitted by a source and to generate acceleration measurements in response to sensing the acceleration wave, wherein the source is associated with the body part of a subject; and a processing device communicatively coupled to the motion sensor, the processing device configured to: receive the acceleration measurements; determine a location of the source using a location of the motion sensor and the acceleration measurements; and image the body part of the subject using the determined location of the source and the acceleration measurements.

In an Example 2, the system of Example 1, wherein the motion sensor comprises a plurality of motion sensors positioned at different locations relative to the source and wherein each motion sensor generates acceleration measurements used to image the body part.

In an Example 3, the system of any of Examples 1-2, wherein, to determine the location of the source, the processing device is configured to: determine an original amplitude of the acceleration wave; and determine the location of the source using the original amplitude.

In an Example 4, the system of any of Examples 1-3, wherein the processing device is configured to: apply band-pass filters to the acceleration wave to produce a plurality of acceleration band measurements; and determine the location of the source using the plurality of acceleration band measurements.

In an Example 5, the system of any of Examples 1-4, wherein the acceleration wave is sensed at a plurality of times and wherein, to image the body part, the processing device is configured to: determine an acceleration matrix of the acceleration wave using the determined location of the source; determine a velocity matrix using the acceleration matrix, the acceleration wave sensed at a first time, and the acceleration wave sensed at a second time; determine a position using the velocity matrix and the acceleration wave sensed at a third time; and image the body part of the subject using the position matrix.

In an Example 6, the system of any of Examples 1-5, wherein the source of the sound is the body part.

In an Example 7, the system of any of Examples 1-6, wherein the source of the sound is a thumper and the acceleration wave propagates through the body part before being sensed by the motion sensor.

In an Example 8, the system of any of Examples 1-7, wherein, to image the body part of the subject, the processing device is configured to produce a structural image of the part.

In an Example 9, the system of Example 8, wherein, to produce a structural image, the processing device is configured to: determine a dampening coefficient matrix; and produce the structural image using the dampening coefficient matrix.

In an Example 10, a method for imaging a body part comprises: receiving acceleration measurements associated with a body part of a subject, the acceleration measurements produced by a motion sensor that sensed an acceleration wave emitted by a source; determining a location of the source using a location of the motion sensor and the acceleration measurements; and imaging the body part of the subject using the determined location of the source and the acceleration measurements.

In an Example 11, the method of Example 10, wherein determining the location of the source comprises: determining an original amplitude of the acceleration wave; and determining the location of the source using the original amplitude.

In an Example 12, the method of any of Examples 10-11, the method further comprising: applying band-pass filters to the acceleration wave to produce a plurality of acceleration band measurements; and determining the location of the source using the plurality of acceleration band measurements.

In an Example 13, the method of any of Examples 10-12, wherein the acceleration wave is sensed by the motion sensor at a plurality of times, and wherein imaging the body part comprises: determining an acceleration matrix of the acceleration wave using the determined location of the source; determining a velocity matrix using the acceleration matrix and the acceleration wave sensed at a first time and the acceleration wave sensed at a second time; determining a position using the velocity matrix and the acceleration wave sensed at a third time; and imaging the body part of the subject using the position matrix.

In an Example 14, the method of any of Examples 10-13, wherein the source of the sound is the body part.

In an Example 15, the method of any of Examples 10-14, the method further comprising: determining a dampening coefficient matrix; and producing a structural image of the body part using the dampening coefficient matrix.

In an Example 16, a system for imaging a body part, comprising: a motion sensor configured to sense an acceleration wave emitted by a source and to generate acceleration measurements in response to sensing the acceleration wave, wherein the source is associated with the body part of a subject; and a processing device communicatively coupled to the motion sensor, the processing device configured to: receive the acceleration measurements; determine a location of the source using a location of the motion sensor and the acceleration measurements; and image the body part of the subject using the determined location of the source and the acceleration measurements.

In an Example 17, the system of Example 16, wherein the motion sensor comprises a plurality of motion sensors positioned at different locations relative to the source and wherein each motion sensor generates acceleration measurements used to image the body part.

In an Example 18, the system of Example 16, wherein, to determine the location of the source, the processing device is configured to: determine an original amplitude of the acceleration wave; and determine the location of the source using the original amplitude.

In an Example 19, the system of Example 16, wherein the processing device is configured to: apply band-pass filters to the acceleration wave to produce a plurality of acceleration band measurements; and determine the location of the source using the plurality of acceleration band measurements.

In an Example 20, the system of Example 16, wherein the acceleration wave is sensed at a plurality of times and wherein, to image the body part, the processing device is configured to: determine an acceleration matrix of the acceleration wave using the determined location of the source; determine a velocity matrix using the acceleration matrix, the acceleration wave sensed at a first time, and the acceleration wave sensed at a second time; determine a position using the velocity matrix and the acceleration wave sensed at a third time; and image the body part of the subject using the position matrix.

In an Example 21, the system of Example 16, wherein the source of the sound is the body part.

In an Example 22, the system of Example 16, wherein the source of the sound is a thumper and the acceleration wave propagates through the body part before being sensed by the motion sensor.

In an Example 23, the system of Example 16, wherein, to image the body part of the subject, the processing device is configured to produce a structural image of the part.

In an Example 24, the system of Example 23, wherein to produce a structural image, the processing device is configured to: determine a dampening coefficient matrix; and produce the structural image using the dampening coefficient matrix.

In an Example 25, a method for imaging a body part comprises: receiving acceleration measurements associated with a body part of a subject, the acceleration measurements produced by a motion sensor that sensed an acceleration wave emitted by a source; determining a location of the source using a location of the motion sensor and the acceleration measurements; and imaging the body part of the subject using the determined location of the source and the acceleration measurements.

In an Example 26, the method of Example 25, wherein the motion sensor comprises a plurality of motion sensors positioned at different locations relative to the source and wherein each motion sensor generates acceleration measurements used to image the body part.

In an Example 27, the method of Example 25, wherein determining the location of the source comprises: determining an original amplitude of the acceleration wave; and determining the location of the source using the original amplitude.

In an Example 28, the method of Example 25, the method further comprising: applying band-pass filters to the acceleration wave to produce a plurality of acceleration band measurements; and determining the location of the source using the plurality of acceleration band measurements.

In an Example 29, the method of Example 25, wherein the acceleration wave is sensed by the motion sensor at a plurality of times and wherein imaging the body part comprises: determining an acceleration matrix of the acceleration wave using the determined location of the source; determining a velocity matrix using acceleration matrix and the acceleration wave sensed at a first time and the acceleration wave sensed at a second time; determining a position using the velocity matrix and the acceleration wave sensed at a third time; and imaging the body part of the subject using the position matrix.

In an Example 30, the method of Example 25, wherein the source of the sound is the body part.

In an Example 31, the method of Example 25, wherein the source of the sound is a thumper and the acceleration wave propagates through the body part before being sensed by the motion sensor.

In an Example 32, the method of Example 25, the method further comprising producing a structural image of the body part.

In an Example 33, the method of Example 32, wherein producing a structural image of the body part comprises: determining a dampening coefficient matrix; and producing the structural image using the dampening coefficient matrix.

In an Example 34, a non-transitory computer-readable medium comprising executable instructions that, when executed by one or more processors of a medical system, cause the one or more processors to: determine an acceleration matrix of an acceleration wave using a determined location of the source, wherein the acceleration wave is emitted by a source and wherein the acceleration wave is associated with a body part of a subject; determine a velocity matrix using acceleration matrix and the acceleration wave sensed at a first time and the acceleration wave sensed at a second time; determine a position using the velocity matrix and the acceleration wave sensed at a third time; and image the body part of the subject using the position matrix.

In an Example 35, the non-transitory computer-readable medium of Example 34, comprising executable instructions that when executed by one or more processors of a medical system cause the one or more processors to: determine a dampening coefficient matrix; and produce a structural image of the body part using the dampening coefficient matrix.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
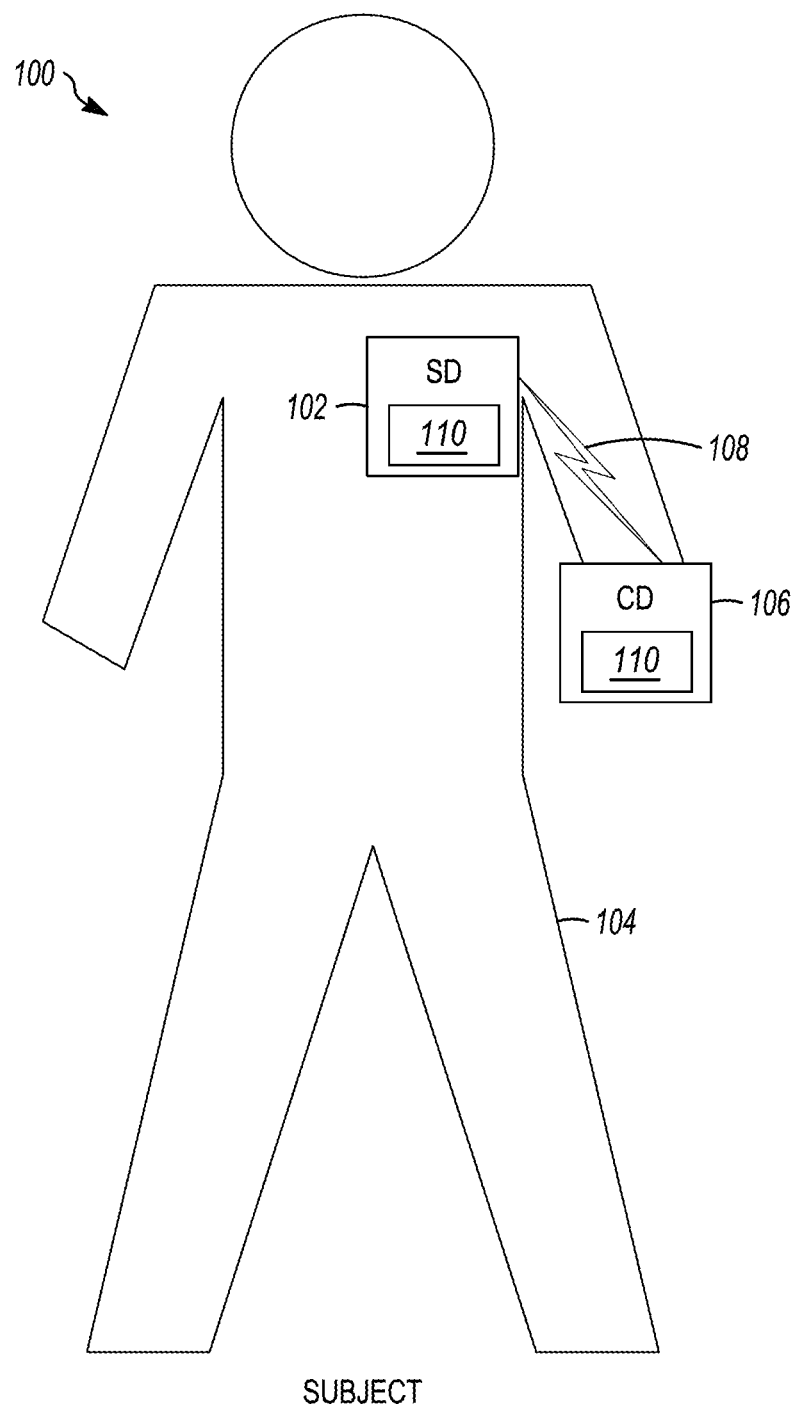
FIG. 1 is a schematic diagram of an illustrative physiological imaging system, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

A "heart sound," as the term is used herein, includes audible and inaudible mechanical vibrations caused by cardiac activity that can be sensed with a motion sensor. Accordingly, when a mechanical sensor such as a motion sensor is used to sense the heart sounds, the scope of energy included in the sensed "acoustic signal" extends to energies associated with such mechanical vibrations. Additionally or alternatively, the motion sensor can be used to sense mechanical vibrations caused by sounds produced by a body part other than the heart and/or sense mechanical vibrations caused by sounds produced by a device such as a thumper.

FIG. 1 shows an illustrative imaging system 100, in accordance with embodiments of the disclosure. As shown in FIG. 1, the imaging system 100 includes a sensing device (SD) 102 configured to be positioned adjacent (e.g., on) the body of a subject 104. In embodiments, the imaging system 100 may include a computational device (CD) 106, which is communicatively coupled to the SD 102 via a communication link 108. The subject 104 may be a human, a dog, a pig, and/or any other animal. For example, in embodiments, the subject 104 may be a human patient.

In embodiments, the SD 102 and/or the CD 106 may be used to sense and/or monitor any number of a variety of physiological, device, subjective, and/or environmental parameters associated with the subject 104, using electrical, mechanical, and/or chemical means. For example, the SD 102 and/or the CD 106 may include sensors or circuitry for detecting sounds, respiratory system signals, cardiac system signals, and/or signals related to patient activity. To do so, the SD 102 and/or the CD 106 may include sensing components such as, for example, one or more surface electrodes configured to obtain an electrocardiogram (ECG), one or more motion sensors configured to detect motion associated with the subject 104, one or more respiratory sensors configured to obtain respiration information, one or more environmental sensors configured to obtain information about the external environment (e.g., temperature, air quality, humidity, carbon monoxide level, oxygen level, barometric pressure, light intensity, sound, and/or the like) surrounding the subject 104, and/or the like. In embodiments, the SD 102 and/or the CD 106 may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

In embodiments, the sounds capable of being detected by the SD 102 and/or the CD 106 may be, but are not limited to, heart sounds, sounds produced by an organ other than the heart, sounds produced by a thumper and/or the like. To detect sounds, the SD 102 and/or the CD 106 may include one or more motion sensors 110. That is, the SD 102 and/or the CD 106 may be configured to use the motion sensor 110 to generate heart sound data, sound data from organs other than the heart (e.g., respiration data), and/or other physiological data. Heart sound data includes information associated with heart sounds such as, for example, identifications of heart sounds, a heart sound signal extracted from an acceleration signal, classifications of heart sounds, statistics or other derived information associated with heart sounds, physiological parameters determined based on heart sounds, and/or the like. Similarly, respiration data includes information associated with respiration such as, for example, identifications of respiratory events and/or stages, a respiration signal extracted from an acceleration (or heart sound) signal, classifications of respiratory events, statistics or other derived information associated with respiration, physiological parameters determined based on respiration information, and/or the like.

In embodiments, the motion sensor 110 may be configured to generate an acceleration signal and/or acceleration data, which may include the acceleration signal, information derived from the acceleration signal, and/or the like. In embodiments, the acceleration data includes acceleration measurements associated with movement of the SD 102 and/or the CD 106. In embodiments, the motion sensor 110 may be, or include, any motion sensor known in the art of and configured to generate measurements associated with its motion. A "motion sensor," as used herein, may be, or include, any type of accelerometer, gyroscope, inertial measurement unit (IMU), and/or any other type of sensor or combination of sensors configured to measure changes in acceleration, angular velocity, and/or the like. In embodiments, the motion sensor 110 may include multiple motion sensors and may be disposed in multiple, different locations on the subject 104.

In embodiments, most smartphones currently include motion sensors configured to generate acceleration data associated with three-dimensional movement of the smartphone (which, in embodiments, may be the SD 102 and/or the CD 106). The inventors have discovered that conventional smartphone motion sensors may be used for detecting heart sounds when the smartphone is positioned in contact with a subject's body in a target region. According to embodiments, a target region is a region in which heart sound signals may be obtained using a motion sensor. That is, for example, when a subject is lying on his or her back, a target region may include the subject's torso or a portion thereof (e.g., the chest); whereas, when a subject is lying on his or her stomach, the target region may include the subject's back. A target location may include any location within a target region and/or a specified location within a target location. According to various embodiments, the target region of a subject may be identified by analyzing acceleration data obtained from the motion sensor to determine, for a given location, whether heart sounds are able to be detected using the motion sensor.

Additionally or alternatively, sensors and associated circuitry (e.g., the motion sensor 110) may be incorporated in connection with the SD 102 and/or CD 106 for detecting one or more body movement or body posture and/or position related signals. For example, the motion sensor 110 and/or GPS device may be employed to detect patient activity, patient location, body orientation, and/or torso position. Derived parameters may also be monitored using the SD 102 and/or CD 106.

The SD 102 and/or the CD 106 may be configured to automatically gather data, gather data upon request (e.g., input provided by the subject, a clinician, another device, and/or the like), and/or any number of various combinations and/or modifications thereof. The SD 102 may be configured to store data related to the physiological, device, environmental, and/or subjective parameters and/or transmit the data to any number of other devices (e.g., CD 106) in the system 100.

In embodiments, the SD 102 and/or the CD 106 may be configured to analyze data and/or act upon the analyzed data. For example, the SD 102 and/or the CD 106 may be configured to image a body part of the subject 104 based on the monitored data, modify therapy, perform additional monitoring, and/or provide alarm indications based on the analysis of the data, as explained in more detail below in relation to FIG. 2. In embodiments, the SD 102 and/or the CD 106 may be any type of device having data analysis capabilities such as, for example, a smartphone, a tablet, a notebook, or other portable computing device. In embodiments, the CD 106 may be a separate device from the SD 102. Alternatively, the SD 102 may be integrated into the CD 106. Additionally or alternatively, while one SD 102 and one CD 106 are depicted in FIG. 1, embodiments may include more than one SD 102 and/or more than one CD 106.

In embodiments, the monitoring and/or analyzing functions described above may be allocated between the SD 102 and the CD 106. For example, the SD 102 may primarily perform the monitoring functions described above and the CD 106 may primarily perform the analyzing functions describe above. In furtherance of this allocation, In embodiments, the SD 102 and/or the CD 106 may be configured to provide therapy. To do so, the SD 102 and/or the CD 106 may include any number of different therapy components such as, for example, a defibrillation component, a drug delivery component, a neurostimulation component, a neuromodulation component, a temperature regulation component, and/or the like. In embodiments, the SD 102 and/or the CD 106 may include limited functionality, e.g., defibrillation shock delivery and communication capabilities, with arrhythmia detection, classification and/or therapy command/control being performed by a separate device. For example, the SD 102 and/or the CD 106 may be configured to communicate with implanted stimulation devices, infusion devices, and/or the like, to facilitate delivery of therapy.

The SD 102 and/or the CD 106 may be, include, or be included in a medical device (external and/or implanted) that may be configured to deliver therapy. Therapy may be provided automatically and/or upon request (e.g., an input by the subject 104, a clinician, another device or process, and/or the like). The SD 102 and/or the CD 106 may be programmable in that various characteristics of their sensing, therapy (e.g., duration and interval), and/or communication may be altered by communication between the SD 102 and the CD 106 and/or other components of the system 100.

According to embodiments, the SD 102 and/or the CD 106 may include any type of medical device, any number of different components of an implantable or external medical system, a mobile device, a mobile device accessory, and/or the like. That is, for example, the SD 102 and/or the CD 106 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104. In various embodiments, the SD 102 and/or the CD 106 may include both defibrillation and pacing/CRT capabilities (e.g., a CRT-D device). In embodiments, the SD 102 and/or the CD 106 may be implanted subcutaneously within an implantation location or pocket in the patient's chest or abdomen and may be configured to monitor (e.g., sense and/or record) physiological parameters associated with the patient's heart. In embodiments, the SD and/or the CD 106 may be an implantable cardiac monitor (ICM) (e.g., an implantable diagnostic monitor (IDM), an implantable loop recorder (ILR), etc.)

configured to record physiological parameters such as, for example, one or more cardiac electrical signals, heart sounds, heart rate, blood pressure measurements, oxygen saturations, and/or the like.

In embodiments, the SD and/or the CD 106 may include a mobile device accessory such as, for example, a device having an electrocardiogram (ECG) module. An ECG module may include any hardware, software, and/or firmware configured to generate ECG data (e.g., ECG measurements, estimated ECG measurements, information about ECG measurements, information derived from ECG measurements, etc.). The SD and/or the CD 106 may include, for example, an ECG sensor assembly such as, for example, the Kardia Mobile device available from AliveCor, of Mountain View, California, USA, which works in conjunction with an app that may be considered to be part of the ECG module. In embodiments, the SD 102 and/or the CD 106 may include, for example, a smart watch such as, for example, a Fitbit, available from Fitbit, Inc., of San Francisco, California, USA. In this manner, the ECG module may include components of a CD 106 and/or the SD 102.

In various embodiments, the SD 102 and/or the CD 106 may be a device that is configured to be portable with the subject 104, e.g., by being integrated into a vest, belt, harness, sticker; placed into a pocket, a purse, or a backpack; carried in the subject's hand; and/or the like, or otherwise operatively (and/or physically) coupled to the subject 104. The SD 102 and/or the CD 106 may be configured to monitor (e.g., sense and/or record) physiological parameters associated with the subject 104 and/or provide therapy to the subject 104. For example, the SD 102 and/or the CD 106 may be, or include, a wearable cardiac defibrillator (WCD) such as a vest that includes one or more defibrillation electrodes In embodiments, the SD 102 may be operatively coupled to the subject 104, and the SD 102 and the CD 106 may be configured to communicate with one another over the communication link 108. In embodiments, the communication link 108 may be, or include, a wired link (e.g., a link accomplished via a physical connection) and/or a wireless communication link such as, for example, a short-range radio link, such as Bluetooth, IEEE 802.11, near-field communication (NFC), WiFi, a proprietary wireless protocol, and/or the like. The term "communication link" may refer to an ability to communicate some type of information in at least one direction between at least two devices, and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the SD 102 and the CD 106, and/or indirect communications that travel between the SD 102 and the CD 106 via at least one other device (e.g., a repeater, router, hub, and/or the like). The communication link 108 may facilitate uni-directional and/or bi-directional communication between the SD 102 and the CD 106. Data and/or control signals may be transmitted between the SD 102 and the CD 106 to coordinate the functions of the SD 102 and/or the CD 106. In embodiments, subject data may be downloaded from one or more of the SD 102 and the CD 106 periodically or on command. The clinician and/or the subject may communicate with the SD 102 and/or the CD 106, for example, to acquire subject data or to initiate, terminate and/or modify sensing and/or computation.

The illustrative cardiac monitoring system 100 shown in FIG. 1 is not intended to suggest any limitation as to the scope of use or functionality of embodiments of the present disclosure. The illustrative cardiac monitoring system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein.

Various components depicted in FIG. 1 may operate together to form the monitoring system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Natick Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Figure 2:
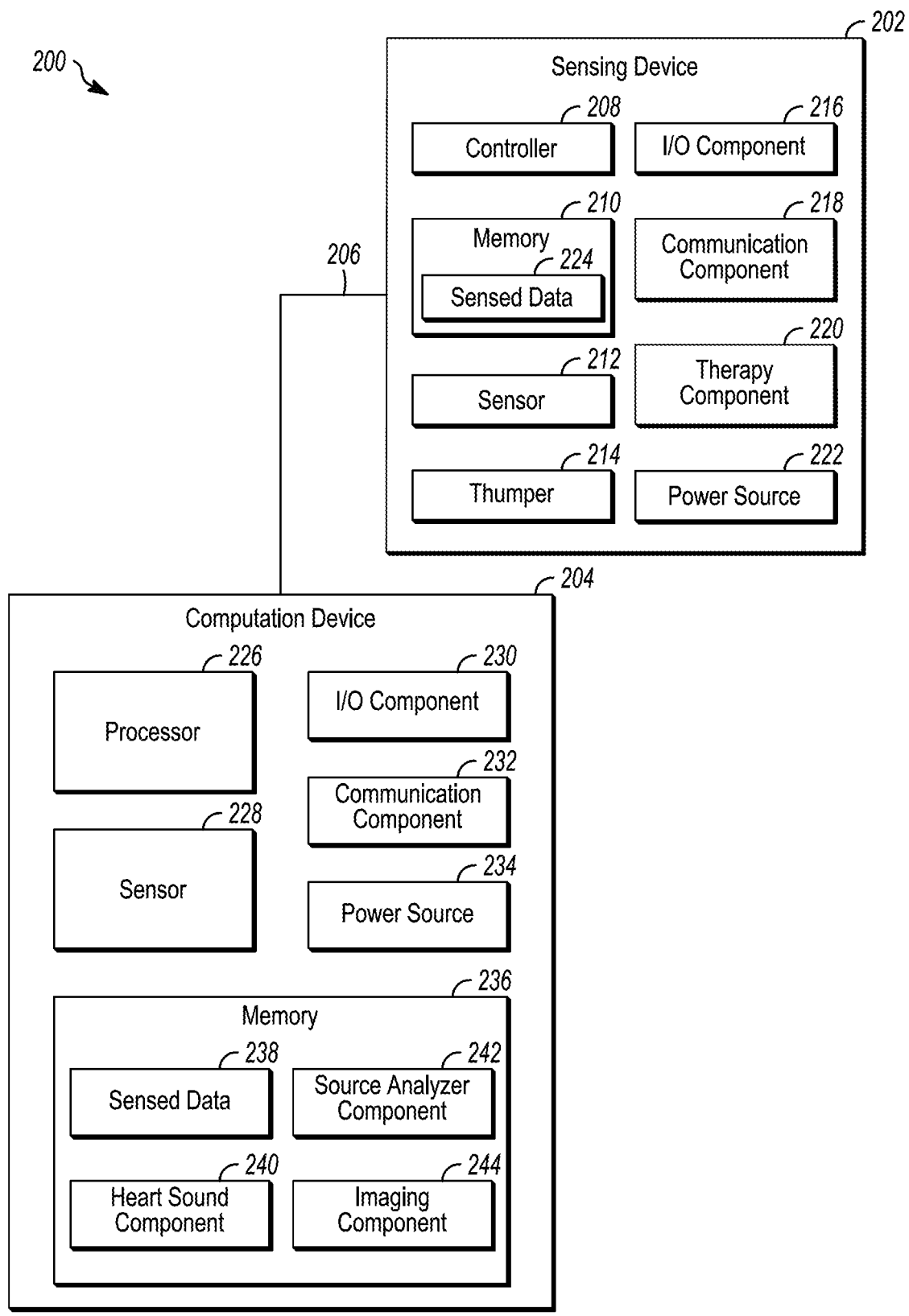
FIG. 2 is a block diagram depicting an illustrative operating environment, in accordance with embodiments of the subject matter disclosed herein.

FIG. 2 is a block diagram depicting an illustrative operating environment 200, in accordance with embodiments of the subject matter disclosed herein. According to embodiments, the operating environment 200 may be, be similar to, include, be included in, or correspond to the system 100 depicted in FIG. 1. As shown in FIG. 2, the illustrative operating environment 200 includes a sensing device (SD) 202 configured to communicate with a computation device (CD) 204 via a communication link 206. In embodiments, the operating environment 200 may include the SD 202 without including a CD 204, include the CD 204 without including the SD 202, and/or include another device. Additionally or alternatively, the operating environment 200 may include more than one SD 202 and/or more than one CD 204. According to embodiments, the SD 202 may be, be similar to, include, or be included in the SD 102 depicted in FIG. 1; the CD 204 may be, be similar to, include, or be included in the CD 106 depicted in FIG. 1; and, the communication link 206 may be, be similar to, include, or be included in the communication links 108 depicted in FIG. 1.

According to embodiments illustrated in FIG. 2, the SD 202 includes a controller 208, a memory 210, a sensor 212, a thumper 214, an input/output (I/O) component 216, a communication component 218, a therapy component 220, and/or a power source 222.

The controller 208 may include, for example, a processing unit, a pulse generator, and/or the like. The controller 208 may be any arrangement of electronic circuits, electronic components, processors, program components and/or the like configured to store and/or execute programming instructions, to direct the operation of the other functional components of the SD 202 (e.g., to direct the sensor 212 to sense sounds and/or to direct the thumper 214 to emanate a sound), to perform processing on any sounds sensed by the sensor 212, to direct the therapy component 220 to provide a therapy, and/or the like, and may be implemented, for example, in the form of any combination of hardware, software, and/or firmware.

In embodiments, the controller 208 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the controller 208 may include a processing unit configured to communicate with memory 210 to execute computer-executable instructions stored in the memory 210. Although the controller 208 is referred to herein in the singular, the controller 208 may be implemented in multiple instances, distributed across multiple sensing devices, instantiated within multiple virtual machines, and/or the like.

The controller 208 may also be configured to store information in the memory 210 and/or access information from the memory 210. For example, the controller 208 may be configured to store data obtained by the sensor 212 as sensed data 224 in memory 210.

In embodiments, the memory 210 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

Computer-executable instructions stored on memory 210 may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

In embodiments, the sensor 212 may sense at one or more times various sounds, physiological and/or environmental parameters, which may then be saved as sensed data 224 on memory 210 and/or transmitted to the CD 204. In embodiments where heart sounds are sensed by the sensor 212, the sensed data 24 may include information associated with heart sounds such as, for example, identifications of heart sounds, classifications of heart sounds, statistics associated with heart sounds, physiological parameters derived from heart sound data, and/or the like. In embodiments, the sensor 212 may be, include, or be included within a motion sensor.

The environmental parameters may include particulates, ultraviolet light, volatile organic compounds, and/or the like in the environment. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like.

The sounds sensed by the sensor 212 may be associated with a subject (e.g., the subject 104) by travelling through tissue of a subject and then sensed by the sensor 212. The sounds associated with a subject may be used by the SD 202 and/or the CD 204 to image a body part of a subject. For example, the sounds travelling through a subject will be attenuated, which can then be used to create a position matrix and/or a structural image, as explained below.

Additionally or alternatively, location data indicative of the location of the sensor 212 may be saved as sensed data 224 and/or transmitted to the CD 204. The location of the sensor 212 may be used to image a body part of a subject, as explained below. While one sensor 212 is depicted as being included in the SD 202, the SD 202 may include multiple sensors 212 that are arranged on, potentially, different locations of a subject (e.g., the subject 104).

To sense various sounds, physiological and/or environmental parameters, the sensor 212 may include temperature sensors (e.g., thermocouples or thermistors), barometers, acoustic sensors, pressure sensors, optical sensors, motion or impact sensors (e.g., accelerometers, gyroscopes, inertial measuring units (IMUs)), strain sensors, Doppler systems, chemical sensors, ultrasound sensors, and/or the like, in any number of various types of configurations. The foregoing sensors allow the SD 202 to be capable of sensing and recording parameters such as, for example, organ and non-organ sounds, patient movement, posture, respiratory cycles, and/or the like. As stated above and described below in relation to FIG. 2, the output from the sensor 212 may be used to image a body part of a subject. In addition, the output from the sensor 212 may also be used in classification, therapy selection, trigger event detection, and/or the like.

In embodiments, the thumper 214 may be configured to generate one or more sounds. For example, the sounds may include short bursts like thumps The sounds generated by the thumper 214 may be associated with a subject (e.g., the subject 104) by travelling through tissue of the subject and then being sensed by a sensor (e.g., the sensor 212). To generate the sounds, the thumper 214 may include any number of electrical circuits, electronic components, processors, program components and/or the like.

The I/O component 216 may include and/or be coupled to a user interface configured to present information to a user or receive indication from a user. For example, the I/O component 216 may include and/or be coupled to a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like. In embodiments, the I/O component 216 may be used to present and/or provide an indication of any of the data sensed and/or produced by the SD 202.

The communication component 218 may be configured to communicate (i.e., send and/or receive signals) with the CD 204 and/or other devices. In embodiments, the communication component 218 may be configured to send sensed data 224 to the CD 204 in response to sensing one or more sounds produced by an organ and/or produced by the thumper 214. Additionally or alternatively, the communication component 218 may be configured to receive signals from the CD 204 to, for example, supplement the sensed data 224 sensed by the sensor 212. The communication component 218 may include, for example, circuits, program components, and one or more transmitters and/or receivers for communicating wirelessly with one or more other devices such as, for example, the CD 204. According to various embodiments, the communication component 218 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 218 may include any combination of hardware, software, and/or firmware configured to facilitate establishing, maintaining, and using any number of communication links.

The therapy component 220 may be configured to delivery therapy in response to one or more sensed and/or derived signals. In embodiments, the therapy component 220 may include any number of different therapy components such as, for example, a drug delivery component, an inhaler component, a nebulizer component, defibrillation component, a neurostimulation component, a neuromodulation component, a temperature regulation component, and/or the like.

The power source 222 provides electrical power to the other operative components (e.g., the controller 208, the memory 210, the sensor 212, the I/O component 216, the communication component 218, and/or the therapy component 220), and may be any type of power source suitable for providing the desired performance and/or longevity requirements of the SD 202. In various embodiments, the power source 222 may include one or more batteries, which may be rechargeable (e.g., using an external energy source). For example, in embodiments, the CD 204 and/or another device may be used to charge the power source 222, transfer power to the power source 222 and/or the like. The power source 222 may include one or more capacitors, energy conversion mechanisms, and/or the like. Additionally or alternatively, the power source 222 may harvest energy from a subject (e.g., the subject 104) (e.g. motion, heat, biochemical) and/or from the environment (e.g. electromagnetic). Additionally or alternatively, the power source 222 may harvest energy from an energy source connected to the body, for example, a shoe may receive energy from impact and send the received energy to a power source 222 of the SD 202.

As shown in FIG. 2, the CD 204 includes a processor 226, a sensor 228, an I/O component 230, a communication component 232, a power source 234, and/or a memory 236.

The processer 226 may include, for example, a processing unit, a pulse generator, and/or the like. The processer 226 may be any arrangement of electronic circuits, electronic components, processors, program components and/or the like configured to store and/or execute programming instructions, to direct the operation of the other functional components of the CD 204, to image a body part of a subject using sounds, and/or perform any number of other functions such as, for example, perform ECG detection, EEG detection, EMG detection, arrhythmia detection, respiratory functionality detection, and/or classification algorithms, to store physiologic data obtained by the sensor 228 as sensed data 238 on the memory 236, and/or the like, and may be implemented, for example, in the form of any combination of hardware, software, and/or firmware.

In embodiments, the processer 226 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the processer 226 may include a processing unit configured to communicate with memory to execute computer-executable instructions stored in the memory. Although the processer 226 is referred to herein in the singular, the processer 226 may be implemented in multiple instances, distributed across multiple computing devices, instantiated within multiple virtual machines, and/or the like.

The processer 226 may also be configured to store information in the memory 236 and/or access information from the memory 236. The processer 226 may execute instructions and perform desired tasks as specified by computer-executable instructions stored in the memory 236. In embodiments, for example, the processer 226 may be configured to instantiate, by executing instructions stored in the memory 236, a heart sound (HS) component 240, a source analyzer component 242, an imaging component 244 and/or the like. Additionally or alternatively, the processer 226 may store any sensed data 238 sensed by the sensor 228 to the memory 236. In embodiments, the processor 226 may store any sensed data 224 transmitted to the CD 204 from the SD 202 as sensed data 238 to the memory 236. Additionally or alternatively, if the sensed data 238 is transferred from the CD 204 to another device, the processor 226 may be configured to erase the sensed data 238 from the CD 204 to free-up storage space on the memory 236.

The sensor 228 may sense at one or more times various sounds, physiological and/or environmental parameters, which may then be saved as sensed data 238. The sounds may be produced by an organ (e.g., heart sounds) and/or may be produced by a device (e.g., a thumper 214). In embodiments where heart sounds are sensed by the sensor 228, the sensed data 238 may include information associated with heart sounds such as, for example, identifications of heart sounds, classifications of heart sounds, statistics associated with heart sounds, physiological parameters derived from heart sound data, and/or the like.

The environmental parameters may include particulates, ultraviolet light, volatile organic compounds, and/or the like in the environment. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like.

The sounds sensed by the sensor 228 may be associated with a subject (e.g., the subject 104) by travelling through tissue of a subject and then sensed by the sensor 228. The sounds associated with a subject may be used by the CD 204 to image a body part of a subject. For example, the sounds travelling through a subject will be attenuated, which can then be used to create a position matrix and/or a structural image, as explained below in relation to FIG. 2.

Additionally or alternatively, location data indicative of the location of the sensor 228 may be saved as sensed data 238. The location of the sensor 228 may be used to image a body part of a subject, as explained below. While one sensor 228 is depicted as being included in the CD 204, the CD 204 may include multiple sensors 228 that are arranged on, potentially, different locations of a subject (e.g., the subject 104).

To sense the one or more sounds, environmental parameters and/or physiological parameters, the sensor 228 may include temperature sensors (e.g., thermocouples or thermistors), barometers, acoustic sensors, pressure sensors, optical sensors, motion or impact sensors (e.g., accelerometers, gyroscopes, inertial measuring units (IMUs)), strain sensors, Doppler systems, chemical sensors, ultrasound sensors, and/or the like, in any number of various types of configurations.

In embodiments, the sensed data 238 of the sensor 228 may supplement the sensed data 224 of the sensor 212. For example, the sensor 228 may have a location that is different than the location of the sensor 212. As such, a single source may produce sensed data 238 that is different than the sensed data 224 due to the locations of the sensors 212, 228 and, therefore, different attenuations of the sounds being sensed. As explained below, the different sensed data 224, 238 may facilitate generating a system of equations that can be used to image one or more parts of a subject (e.g., the subject 104) and/or create a structural image of a subject.

The I/O component 230 may include and/or be coupled to a user interface configured to present information to a user or receive indication from a user. For example, the I/O component 230 may include and/or be coupled to a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, a volatile compound release depot, and/or the like. In embodiments, the I/O component 230 may be used to present and/or provide an indication of any of the data sensed and/or produced by the CD 204 and/or the SD 202. For example, the I/O component 230 may be used to present the position matrix and/or the structural image produced by the CD 204 as described below. In embodiments, the I/O component 230 may include one or more visual indicators (e.g., single-color LED lights, multi-color LED lights, a flexible digital display device, and/or the like) configured to provide information to a user (e.g., by illuminating, flashing, displaying data, etc.). Additionally or alternatively, the I/O component 230 may be used to control therapy provided by the SD 202.

The communication component 232 may be configured to communicate (i.e., send and/or receive signals) with the SD 202 and/or any other device. Additionally or alternatively, the communication component 232 may facilitate receiving the sensed data 224 from the SD 202 and/or transmit the sensed data 238 from the CD 204 to the SD 202 and/or to another device for processing and/or storage.

In embodiments, the communication component 232 may include, for example, circuits, program components, and one or more transmitters and/or receivers for communicating wirelessly with one or more other devices such as, for example, the SD 202. According to various embodiments, the communication component 232 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 232 may include any combination of hardware, software, and/or firmware configured to facilitate establishing, maintaining, and using any number of communication links.

The power source 234 provides electrical power to the other operative components (e.g., the processer 226, the sensor 228, the I/O component 230, the communication component 232, and/or the memory 236), and may be any type of power source suitable for providing the desired performance and/or longevity requirements of the CD 204.

In various embodiments, the power source 234 may include one or more batteries, which may be rechargeable (e.g., using an external energy source). The power source 234 may include one or more capacitors, energy conversion mechanisms, and/or the like. Additionally or alternatively, the power source 234 may harvest energy from a subject (e.g., the subject 104) (e.g. motion, heat, biochemical) and/or from the environment (e.g. electromagnetic). Additionally or alternatively, the power source 234 may harvest energy from an energy source connected to the body, for example, a shoe may receive energy from impact and send the received energy to a power source 234 of the CD 204.

In embodiments, the power source 234 may transfer power to the power source 222 using a wireless or non-wireless connection (e.g., via conduction, induction, radio-frequency, etc.). Because the SD 202 may be implanted within a subject and it may be hard to remove the SD 202 from the subject, the longevity of the SD 202 may be increased via power transfer from the CD 204 to the SD 202. Additionally or alternatively, the power source 222 may transfer power to the power source 234 in order to increase the longevity of the CD 204.

In embodiments, the memory 236 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The memory 236 may store instructions that, when executed by the processor 226 cause methods and processes to be performed by the CD 204. That is, for example, the processor 226 may process instructions and/or data stored in the memory 236 to facilitate detection and/or analysis of organ sounds (e.g., heart sounds) and/or non-organ sounds (e.g., produced by the thumper 214).

For example, the processor 226 may instantiate (e.g., from the memory 236) a HS component 240. In embodiments, the HS component 240 may be configured to generate sensed data 238 from the data collected by the sensor 228 by performing any number of different processes such as, for example, filtering, interpolating, and/or the like. In embodiments, the HS component 240 may be configured to standardize the acceleration data before further processing it. Many conventional motion sensors are configured to take measurements in response to a demand for acceleration data and, often, those measurements are taken using sample rates that are dynamically determined based on the movement of the motion sensor and/or the like. Accordingly, acceleration data often is not generated using a fixed sampling rate. Thus, the HS component 240 may be configured to standardize the acceleration data—that is, to perform a process on the acceleration data that changes it into standardized acceleration data, which is acceleration data that has been modified to estimate what the acceleration data would be if it had been generated using a fixed sampling rate. In embodiments, the HS component 240 may be configured to perform a data interpolation process on the acceleration data to generate standardized acceleration data. The interpolation may be configured to generate standardized acceleration data based on templates, internal characteristics of the acceleration data, known information, and/or the like.

According to embodiments, the HS component 240 may be configured to generate heart sound data that can be stored as sensed data 238, based on the acceleration data, by performing a noise reduction process on the standardized acceleration data. In embodiments, performing the noise reduction process on the standardized acceleration data may include performing at least one of: spectral filtering (e.g., by attenuating specified frequencies, frequency bands, etc.), bandpass filtering (e.g., by attenuating frequency bands above and/or below specified thresholds), high pass filtering (e.g., by attenuating frequencies below a specified threshold to remove DC offsets), and/or the like. Attenuating components of a signal, as described herein, may include removing, suppressing, transforming, or otherwise attenuating the component of the signal as is understood by those having skill in the relevant arts. In this manner, noise reduction may be performed by rejecting signal values that are not likely to include heart sound information.

In embodiments, for example, a frequency band and/or threshold corresponding to heart sounds of a subject may be determined using information from the CD 204, the SD 202, and/or the like, and used to filter an acceleration signal (and/or standardized acceleration signal) to attenuate acceleration data that is not associated with heart sounds. It has been discovered, for example, that components of an acceleration signal having a frequency above approximately 200 Hertz are generally not associated with heart sounds. Thus, in embodiments, the HS component 240 may be configured to attenuate the component of the motion sensor signal not associated with heart sounds such as, for example, by attenuating motion sensor data having frequencies above approximately 200 Hertz. In some embodiments, this may be the only filtering process performed on the standardized acceleration signal, while, in other embodiments, other filtering process may be performed in addition to, or in lieu of, this frequency filtering. For example, in embodiments, copies of the motion sensor signal may be band-pass filtered by filters having a band-pass width of 5 Hertz, 10 Hertz, 15 Hertz, 20 Hertz and/or the like. In these embodiments, multiple data bands may be derived from the acceleration signals. Each of these data bands may be used to generate a system of equations used to image a part of subject as explained below.

Additionally or alternatively, the processor 226 may instantiate (e.g., from the memory 236) a source analyzer component 242. In embodiments, the source analyzer component 242 may be configured to determine, based on the sensed data 238, the location of a source producing a sound sensed by the sensor 228. To determine a location of a source, the source analyzer component 242 may solve a system of equations generated using the sensed data 238. For example, in embodiments where the sensed data 238 includes sound data sensed by two sensors 212, 228 at different, respective locations, the following equations may be generated by the source analyzer component 242:

$A = S*(c_1/(d_1+c_1))$, $B = S*(c_1/(d_2+c_1))$, and $D = d_1 + d_2$.

In these equations, A is the amplitude of the sound sensed by a first sensor 212 at a first location, B is the amplitude of the sound sensed by a second sensor 228 at a second location, S is the amplitude of the sound at the source of the sound, $d_1$ is the distance between the first sensor 212 and the source, $d_2$ is the distance between the second sensor 228 and the source, and $c_1$ is a coefficient of dampening applied to the sound as the sound propagates from the source to the first sensor 212 and from the source to the second sensor 228. In embodiments, the location of the source may be assumed to be between the sensors 212, 228. D is then known because the locations of the sensors 212, 228 are known. In addition, because the sensors 212, 228 are sensing the amplitudes at their respective locations, A and B are known. Finally, in embodiments where the sound is travelling through a subject to reach the sensors 212, 228, the value of $c_1$ may be assumed to be the same or similar to a coefficient of dampening of soft tissue, hard tissue and/or an average thereof.

In view of the number of unknown quantities (i.e., $d_1$, $d_2$, and S) being equal to the number of equations (i.e., three equations), the equations may be rearranged and S, which corresponds to the amplitude of the sound at the source, may be solved for according to the following equation: $S=(A*B*(D+2*c_1))/(Bc_1+Ac_1)$. Once S is calculated, $d_1$ and $d_2$ may be calculated using the following equations: $d1=((S*c_1)/A)-c_1$ and $d_2=((S*c_1)/B)-c_1$. After $d_1$ and $d_2$ are calculated, the location of the source S may be determined because, as set forth above, $d_1$ is the distance between the first sensor 212 and the source, $d_2$ is the distance between the second sensor 228 and the source and the locations of the sensors 212, 228 are known.

While the above equations are solved using two sensors 212, 228, the source analyzer component 242 may derive and solve a system of equations using more than two sensors 212, 228. Additionally or alternatively, the heart sound component 240 and/or the source analyzer component 242 may divide the sound data included in the sensed data 238 into different spectrum bands in order to derive a greater number of equations and, in turn, solve the equations. In embodiments, the greater number of derived equations may facilitate determining dampening coefficients that are not assumed to be constant in different directions. That is, as set forth above, the dampening coefficient between the first sensor 212 and the second sensor 228 is assumed to be the same $c_1$. In embodiments where more than two sensors are used to sense a sound and/or where the acceleration signals of the sound are divided into multiple spectrum bands, more than three equations can be derived. As such, the dampening coefficient between the first sensor 212 and the source may be assumed to be different than the dampening coefficient between the second sensor 228 and the source. Then, the different dampening coefficients can be solved for using the equations derived from the sound data sensed by more than two sensors and/or the multiple spectrum bands of the acceleration signals.

The imaging component 244 may image a body part of the subject, which the sound at least partially propagates through, based on the sensed data 238 and the location of the source determined by the source analyzer component 242. That is, once the location of the source is determined by the source analyzer component 242, the imaging component 244 may construct an acceleration matrix for the sound wave. The acceleration matrix may indicate the acceleration measurements of the sound wave at different locations. Stated another way, the acceleration matrix may include the acceleration measurements of the sound wave as it emanates away from the source.

Based on the acceleration matrix, the imaging component 244 may determine a velocity matrix. The velocity matrix may include the velocities of the sound wave at different locations. And, the velocities of the sounds waves may be indicative of the velocity of the underling tissue through which the sound wave is propagated. To determine the velocity matrix, the imaging component 244 may use the acceleration data that has been sensed at multiple times by one or both of the sensors 212, 238 and stored as sensed data 238. Based on the acceleration data sensed at multiple times, the imaging component 244 may determine velocities at different locations based on the following equation $v(t)=v(t-1)+a(t)*\Delta t$; $v(t)$ is the velocity of the sound wave at time t, $v(t-1)$ is the velocity of the sound wave at time t−1, $a(t)$ is the acceleration at time t and $\Delta t$ is the change in time between t and t−1. For each acceleration measurement at a respective location of the acceleration matrix, a corresponding velocity may be determined according the recited equation.

In embodiments, a dampening factor may be applied with each successive time point calculation of the above recited equations (or, in embodiments, any number of other equations that may be utilized in addition to, or in lieu of, those described above). For example, due to noise and motion sensor limitations, a set of acceleration signals may not integrate to zero. This may result in noisy residual movement in the velocity matrix, which can adversely affect the position matrix (described below). In embodiments, a dampening factor may be selected based on the model and/or the sensitivity of the sensors so that, e.g., the acceleration signals integrate to zero.

In embodiments, the imaging component 244 may also determine a position matrix based on the velocity matrix and the acceleration data sensed at multiple times. The position matrix may include the positions of the sound wave at different locations. And, the positions of the sounds waves may be indicative of the position of the underling tissue through which the sound wave is propagated. To determine the position matrix, the imaging component 244 may determine positions of the tissue through which the sound wave propagated based on the following equation $x(t)=x(t-1)+v(t)*\Delta t+a(t)*(\Delta t)^2$; where $x(t)$ is the position of the tissue at time t, $x(t-1)$ is the position of the tissue at time t−1, $v(t)$ is the velocity of the tissue, $\Delta t$ is the change in time between t and t−1, and $a(t)$ is the acceleration of the tissue at time t. For each velocity measurement at a respective location of the velocity matrix, a corresponding position may be determined according the recited equation. Once the position matrix is determined, it may be output via the I/O component 232 for analysis by a physician and/or other medical professional, as shown in FIGS. 3A-3D.

Additionally or alternatively, in embodiments where multiple dampening coefficients are determined, the imaging component 244 may determine a structural image of a part of subject. That is, as stated above, dampening coefficients for tissue between different sensors may be determined. Based on the different dampening coefficients, the imaging component 244 may determine a dampening coefficient matrix which is indicative of the dampening coefficients at different locations. Further, each dampening coefficient may be indicative of different types of tissue through which a sound wave is propagating. For example, sounds may be more damped when the sound is travelling through soft tissue than hard tissue. As such, a higher dampening coefficient at a location in the coefficient matrix may indicate soft tissue at the location. Conversely, a lower dampening coefficient at a location in the coefficient matrix may indicate hard tissue at the location. Based on this data, the imaging component 244 may then determine the structural image of the underlying tissue according to the following equation $$SI = \frac{\sum_{i=1}^{T} \text{Coefficients of the Coefficient Matrix}}{T}.$$

Once the structural image is determined, it may be output via the I/O component 232 for analysis by a physician and/or other medical professional.

The coefficients included in the coefficient matrix may be normalized relative to one of the highest coefficients or one of the lowest coefficients. For example, if the sound is travelling through soft tissue, which typically results in a high level of dampening, a coefficient of dampening for the soft tissue may be represented by an integer (e.g., 1) and coefficients of dampening for other types of tissue may be represented by a factor of the integer (e.g., a range from 1.0*integer to 5.0*integer). Additionally or alternatively, if the sound is travelling through hard tissue, which typically results in a low level of dampening, a coefficient of dampening for the hard tissue may be represented by an integer (e.g., 1) and coefficients of dampening for other types of tissue may be represented by a percentage of the integer (e.g., a range from 10%*integer to 100%*integer).

Any number of various components of the operating environment 200 depicted in FIG. 2 may be communicatively coupled via the communication link 206. The communication link 206 may provide for communications between and among various components of the operating environment 200, such as the SD 202 and the CD 204. The communication link 206 may be, be similar to, include, or be included in the communication link 108 depicted in FIG. 1, and/or any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The communication link 306 may include a combination of multiple networks, which may be wired and/or wireless.

Figure 3A:
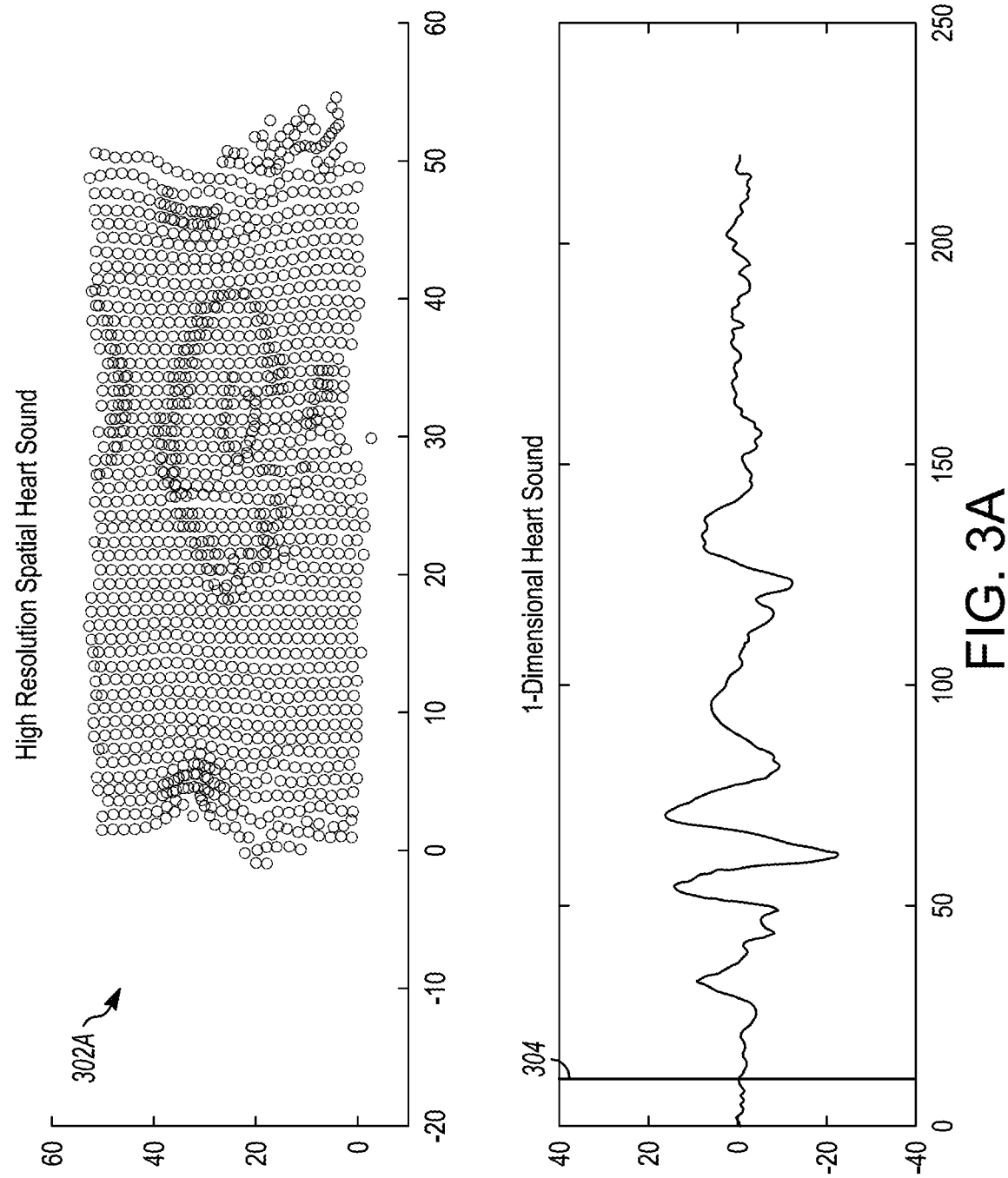
FIGS. 3A-3D depict positional matrices of heart tissue as function of time, in accordance with embodiments of the subject matter disclosed herein.
Figure 3B:
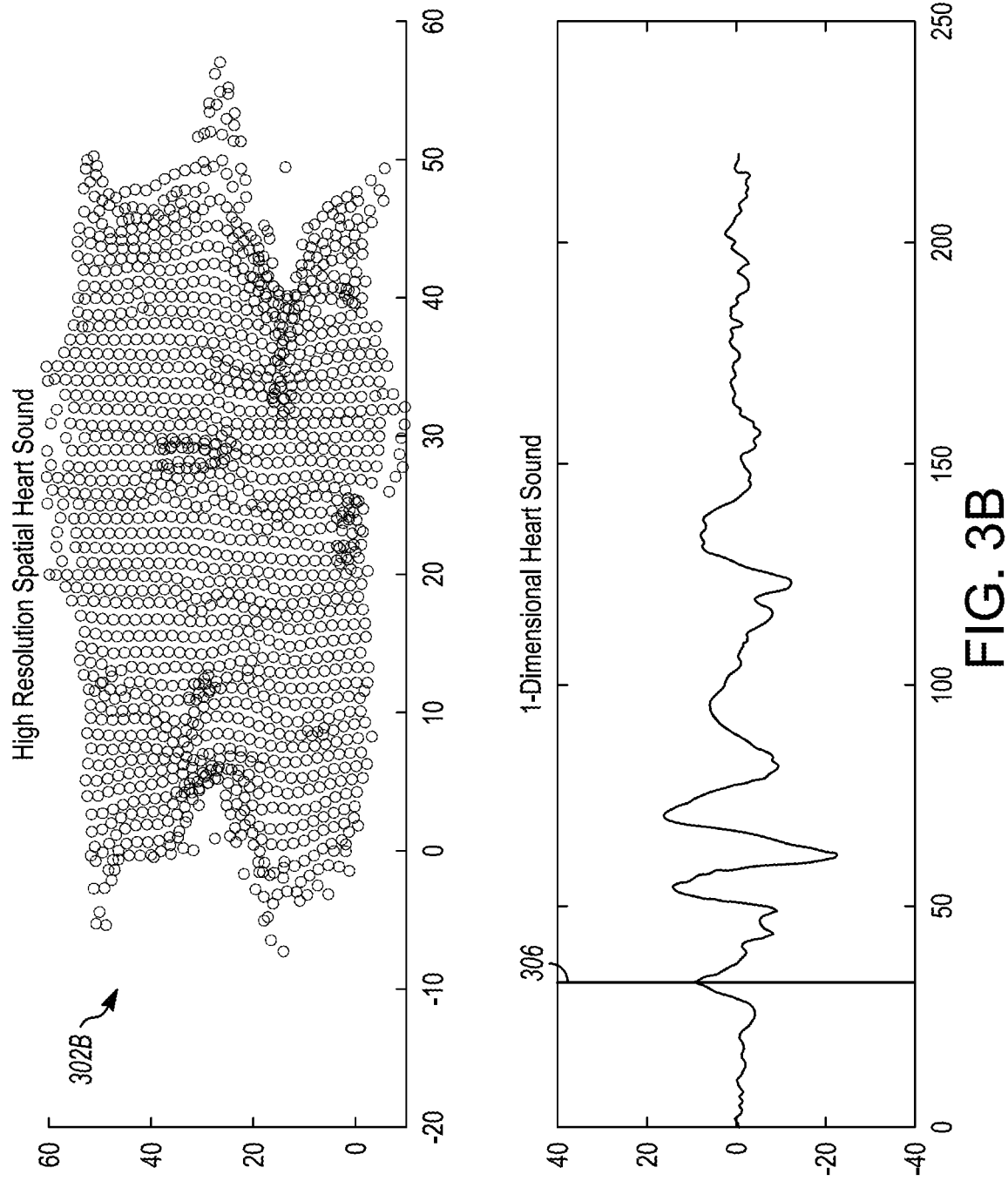
Figure 3C:
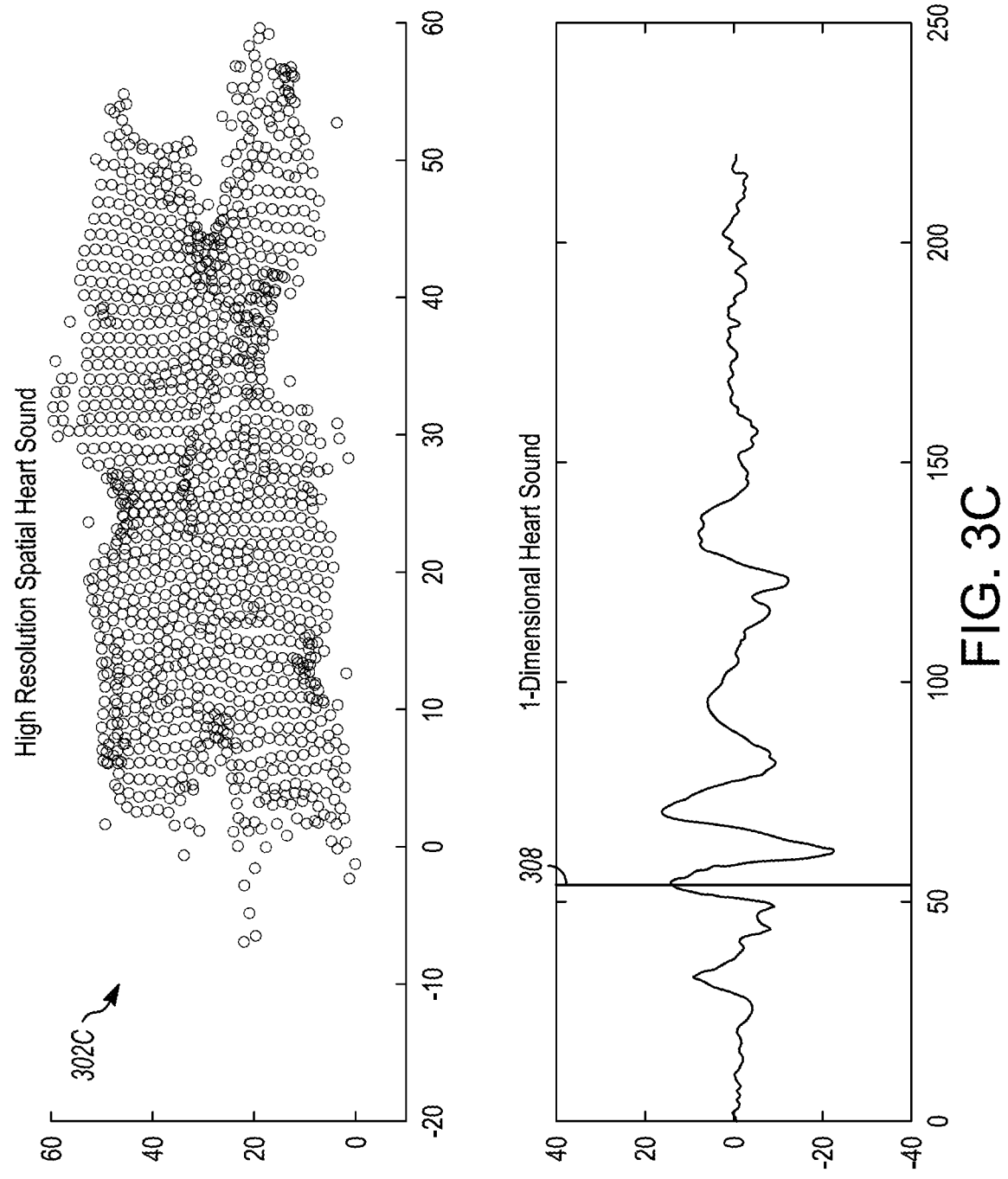
Figure 3D:
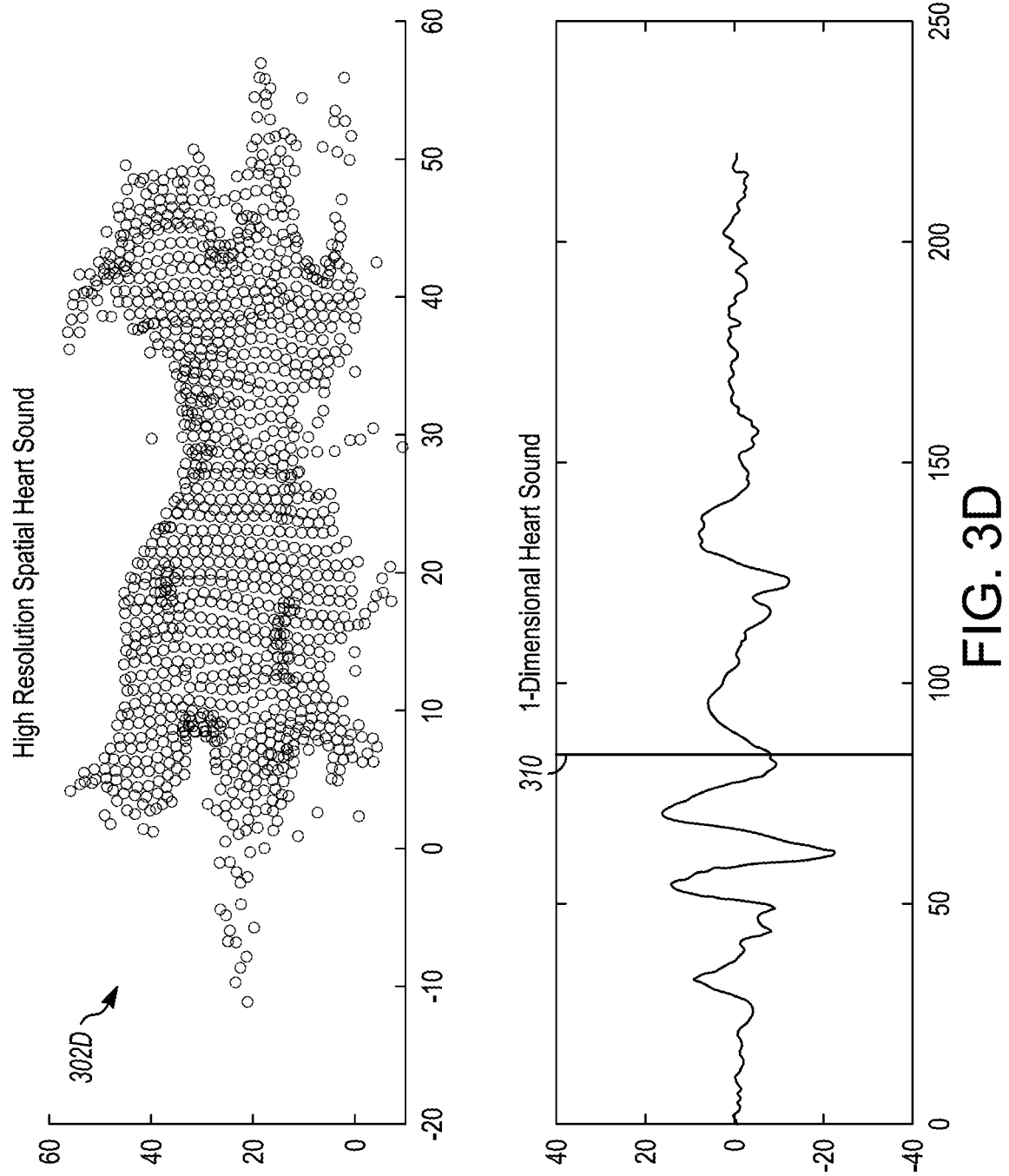

The illustrative operating environment shown in FIG. 2 is not intended to suggest any limitation as to the scope of use or functionality of embodiments of the present disclosure. The illustrative operating environment 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure FIGS. 3A-3D depict positional matrices 302A-302D of heart tissue as function of time, in accordance with embodiments of the present disclosure. That is, each positional matrix 302A-302D includes the positioning of different parts of heart tissue of a subject at different times. For example, FIG. 3A depicts the positional matrix 302A of the heart tissue at time 304; FIG. 3B depicts the positional matrix 302B of the heart tissue at time 306; FIG. 3C depicts the positional matrix 302C of the heart tissue at time 308; and, FIG. 3D depicts the positional matrix 302D of the heart tissue at time 310. Stated another way, FIGS. 3A-3D depict the deformation of the tissue as a function of time.

In embodiments where the tissue is a heart, which are the embodiments illustrated, a physician may determine whether the heart tissue is healthy and functioning normally or unhealthy and functioning abnormally. For example, the different positions of the positional matrices 302A-302D may be mapped to different portions of the heart. Based on the correlation between the positions of the positional matrices 302A-302D, a physician may be able to determine the ventricular contraction, ejection fraction, ventricular stiffness, regurgitation, S4 measurements, and/or aortic stiffness of the subject (e.g., the subject 104). As such, as the heart goes through is rhythm, a physician may determine whether a specific position of the positional matrix deforms (e.g., moves) in a normal manner. If it doesn't, a physician may be able to determine in a non-invasive manner whether there may be an issue with a portion of the heart (e.g., heart wall thickening) that correlates to that position of the positional matrix. As another example, a physician may be able to localize congestive heart sounds based on the positional matrices 302A-302D While the heart tissue is shown as an example in FIGS. 3A-3D, a positional matrix for other organs that produce sounds may be constructed as well. Additionally or alternatively, a thumper (e.g., the thumper 214) may be used to construct a positional matrix for organs that don't produce sounds and/or for other body parts via sounds from the thumper propagating through specific tissue.

Figure 4:
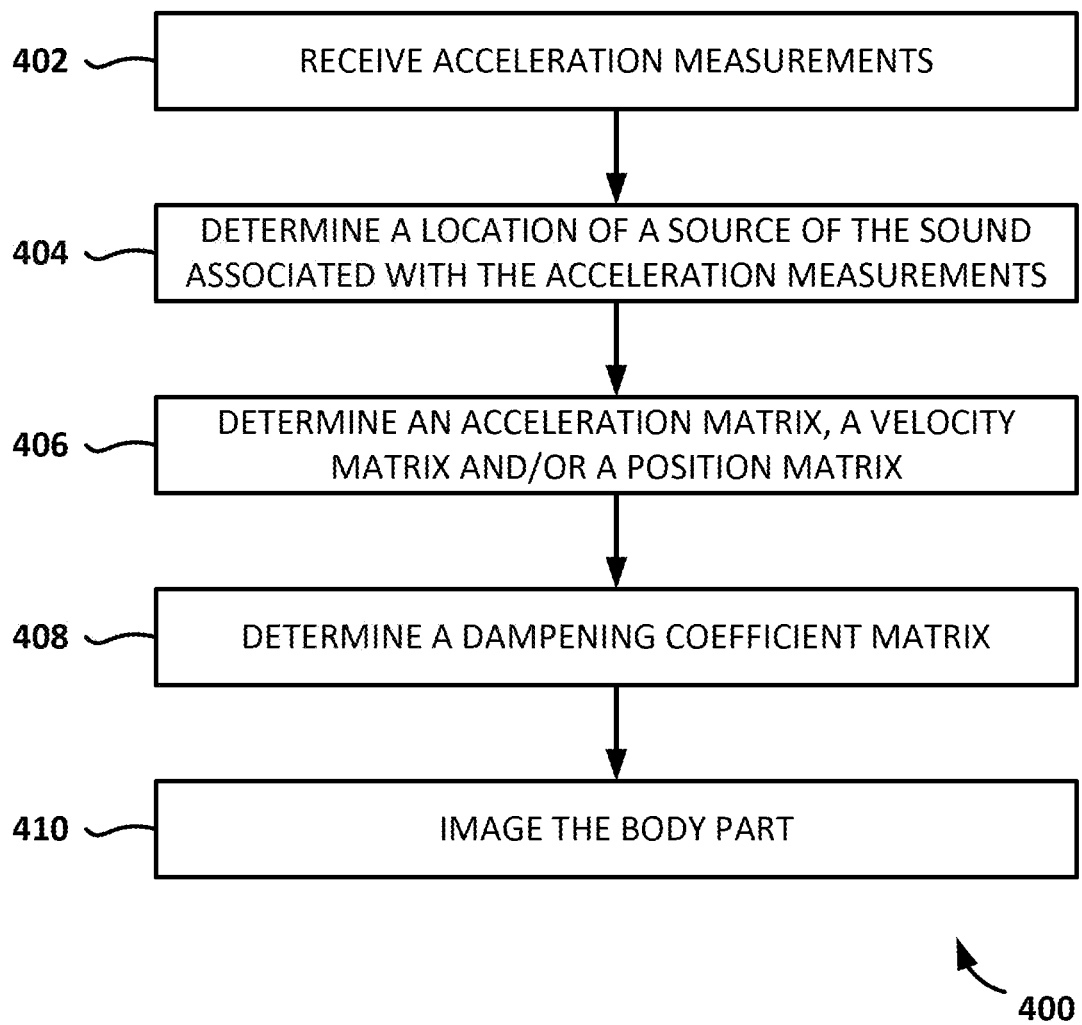
FIG. 4 is a flow diagram of an illustrative method for imaging a body part, in accordance with embodiments of the subject matter disclosed herein.

FIG. 4 is a flow diagram depicting an illustrative method 400 for imaging a body part, in accordance with embodiments of the present disclosure. According to embodiments, the method 400 may be performed by any number of different aspects of components of the system 100 depicted in FIG. 1 and/or the operating environment 200 depicted in FIG. 2. For example, in embodiments, the illustrative method 400 may be performed by a SD 102, 202 and/or a CD 106, 204 having a motion sensor, a processor, and a memory, as described herein.

Embodiments of the method 400 include receiving acceleration measurements (block 402). The acceleration measurements may be the same or similar to the acceleration measurements included in the sensed data 224 and/or the sensed data 238. For example, the acceleration measurements may be produced by one or more sensors (e.g., the motion sensor 110, sensor 212 and/or the sensor 228) after sensing an acceleration wave produced by a sound. In embodiments, the sound may be produced by an organ (e.g., a heart sound) and/or may be produced by a thumper (e.g., the thumper 214). In embodiments, the one or more sensors may be positioned at different locations on the subject. In embodiments, the sound may be associated with the body part by at least partially propagating through the body part of the subject to reach the one or more sensors. In embodiments, one or more band-pass filters may be applied to the acceleration measurements to produce a plurality of acceleration band measurements. The plurality of acceleration band measurements may be used to derive a system of equations, as explained above in relation to FIG. 2.

The method 400 further includes determining a location of a source of the sound associated with the acceleration measurements (block 404). In embodiments, to determine a location of the source, an original amplitude of the acceleration wave may be determined and then based on the original amplitude of the acceleration wave the location of the source may be determined according to the following equations:

$$A = S^*(c_1/(d_1+c_1)),$$

$$B = S^*(c_1/(d_2+c_1)), \text{ and}$$

$$D = d_1 + d_2.$$

In embodiments, as discussed above in relation to FIG. 2, this system of equations may be derived for embodiments using two sensors. Additionally or alternatively, additional equations may be derived when more than two sensors are used to sense the acceleration waves of a sound and/or when the acceleration measurements are divided into a plurality of acceleration band measurements.

As shown in FIG. 4, the method 400 may further include determining an acceleration matrix, a velocity matrix, and/or a position matrix (block 406). In embodiments, the acceleration matrix, the velocity matrix and/or the position matrix may be determined using the same or similar techniques described above in relation to FIG. 2. In embodiments, the acceleration matrix may indicate the acceleration measurements of the sound wave at different locations; the velocity matrix may include the velocities of the sound wave at different locations, which may be indicative of the velocity of the underling tissue through which the sound wave is propagated; and, the position matrix may include the positions of the sound wave at different locations, which may be indicative of the position of the underling tissue through which the sound wave is propagated. The acceleration matrix, the velocity matrix and the position matrix may be determined based on sensing the acceleration wave produced by the sound at a plurality of times.

Additionally or alternatively, the method 400 may include determining a dampening coefficient matrix (block 408). The dampening coefficient matrix may be determined using a derived system of equations. The system of equations used to determine a dampening coefficient matrix may be derived when more than two sensors are used to sense the acceleration waves of the sound and/or when the acceleration measurements are divided into a plurality of acceleration band measurements. In embodiments, the method 400 may further include imaging a body part (block 410). The body part may be imaged using the position matrix. Additionally or alternatively, a structural image of the body part may be produced using the dampening coefficient matrix. To produce the structural image of the body part the following equation may be used:

$$SI = \frac{\sum_{i=1}^{T} \text{Coefficients of the Coefficient Matrix}}{T}.$$

According to embodiments, the method 400 may include any number of other steps, alternative steps, alternative orders of steps, and/or the like.

Various modifications and additions can be made to the exemplary embodiments discussed without departing from the scope of the presently disclosed subject matter. For example, while the embodiments described above refer to particular features, the scope of this disclosure also includes embodiments having different combinations of features and embodiments that do not include all of the described features. Accordingly, the scope of the subject matter disclosed herein is intended to embrace all such alternatives, modifications, and variations as fall within the scope of the claims, together with all equivalents thereof.

We claim:

1. A system for imaging an organ, comprising:
an acceleration sensor configured to sense an acceleration wave emitted by a source and to generate acceleration measurements in response to sensing the acceleration wave, wherein the source is the organ of a subject, wherein the organ is a heart; and
a processing device communicatively coupled to the acceleration sensor, the processing device configured to:
receive the acceleration measurements;
determine a location of the source using a location of the acceleration sensor and the acceleration measurements; and
generate an image of the organ of the subject using the determined location of the source and the acceleration measurements.

2. The system of claim 1, wherein the acceleration sensor comprises a plurality of acceleration sensors positioned at different locations relative to the source and wherein each acceleration sensor generates acceleration measurements used to generate the image of the organ.

3. The system of claim 1, wherein, to determine the location of the source, the processing device is configured to:
determine an original amplitude of the acceleration wave; and
determine the location of the source using the original amplitude.

4. The system of claim 1, wherein the processing device is configured to:
apply band-pass filters to the acceleration wave to produce a plurality of acceleration band measurements; and
determine the location of the source using the plurality of acceleration band measurements.

5. The system of claim 1, further comprising:
a thumper configured to produce a sound wave for the source,
wherein the acceleration wave is indicative of the sound wave propagating through the organ before being sensed by the acceleration sensor.

6. The system of claim 1, wherein the image of the organ comprises at least one of: a position matrix or a structural image of the organ of the subject.

7. The system of claim 6, wherein the acceleration wave is sensed at a plurality of times and wherein, to generate the image of the organ, the processing device is configured to:
determine an acceleration matrix of the acceleration wave using the determined location of the source;
determine a velocity matrix using the acceleration matrix, the acceleration wave sensed at a first time, and the acceleration wave sensed at a second time;
determine the position matrix using the velocity matrix and the acceleration wave sensed at a third time; and
generate the image of the organ of the subject comprising the position matrix.

8. The system of claim 6, wherein to generate the image of the organ, the processing device is configured to:
determine a dampening coefficient matrix; and
produce the structural image using the dampening coefficient matrix.

9. A method for imaging an organ, the method comprising:
receiving acceleration measurements produced by an acceleration sensor that sensed an acceleration wave emitted by a source, wherein the source is the organ of a subject, wherein the organ is a heart;
determining a location of the source using a location of the acceleration sensor and the acceleration measurements; and
generating an image of the organ of the subject using the determined location of the source and the acceleration measurements.

10. The method of claim 9, wherein the acceleration sensor comprises a plurality of acceleration sensors positioned at different locations relative to the source and wherein each acceleration sensor generates acceleration measurements used to generate the image of the organ.

11. The method of claim 9, wherein determining the location of the source comprises:
determining an original amplitude of the acceleration wave; and
determining the location of the source using the original amplitude.

12. The method of claim 9, the method further comprising:
applying band-pass filters to the acceleration wave to produce a plurality of acceleration band measurements; and
determining the location of the source using the plurality of acceleration band measurements.

13. The method of claim 9, wherein receiving the acceleration measurements comprises:
receiving the acceleration measurements produced by the acceleration sensor that sensed the acceleration wave indicative of a sound wave produced by a thumper for the source and propagating through the organ before being sensed by the acceleration sensor.

14. The method of claim 9, wherein generating the image of the organ comprises generating at least one of: a position matrix or a structural image of the organ of the subject.

15. The method of claim 14, wherein the acceleration wave is sensed by the acceleration sensor at a plurality of times and wherein generating the image of the organ comprises:
determining an acceleration matrix of the acceleration wave using the determined location of the source;
determining a velocity matrix using acceleration matrix and the acceleration wave sensed at a first time and the acceleration wave sensed at a second time;
determining the position matrix using the velocity matrix and the acceleration wave sensed at a third time; and
generating the image of the organ of the subject comprising the position matrix.

16. The method of claim 14, wherein generating the image of the organ comprises:
determining a dampening coefficient matrix; and
producing the structural image using the dampening coefficient matrix.

* * * * *